(12) United States Patent
Vaisman et al.

(10) Patent No.: US 7,549,996 B2
(45) Date of Patent: Jun. 23, 2009

(54) TUNNELING NEEDLE DESIGN HAVING AN ON-DEMAND REMOVABLE HUB

(76) Inventors: Julien Vaisman, 52 Philips Beach Ave., Swampscott, MA (US) 01907; Joe I. Ordia, 3 Heathwood La., Chestnut Hill, MA (US) 02467

( * ) Notice: Subject to any disclaimer, the term of this patent is extended or adjusted under 35 U.S.C. 154(b) by 236 days.

(21) Appl. No.: 11/516,818

(22) Filed: Sep. 7, 2006

(65) Prior Publication Data
US 2008/0065028 A1 Mar. 13, 2008

(51) Int. Cl.
*A61F 11/00* (2006.01)
(52) U.S. Cl. .................... 606/108; 604/500
(58) Field of Classification Search ............ 604/164.04, 604/164.07, 272, 164.01, 264, 500; 606/108
See application file for complete search history.

(56) References Cited

U.S. PATENT DOCUMENTS

| | | | |
|---|---|---|---|
| 6,336,914 B1 * | 1/2002 | Gillespie, III | 604/165.01 |
| 6,533,759 B1 * | 3/2003 | Watson et al. | 604/167.02 |
| 2003/0028146 A1 * | 2/2003 | Aves | 604/164.06 |
| 2005/0027282 A1 * | 2/2005 | Schweikert et al. | 604/523 |
| 2005/0261664 A1 * | 11/2005 | Rome et al. | 604/508 |

* cited by examiner

*Primary Examiner*—Nicholas D Lucchesi
*Assistant Examiner*—Theodore J Stigell
(74) *Attorney, Agent, or Firm*—David Prashker, Esq.

(57) ABSTRACT

The present invention provides a medical needle assembly which has a removable at will needle hub for a spinal needle, which can be used to access the epidural or subarachnoid space of the spinal cord. This improvement in spinal needle design allows and facilitates the use of the medical needle for the purposeful creation of a subcutaneous tunnel and the placement of a catheter, or drain, or electrical wire lead which extends to an anatomic location remote from the original surgical incision site.

The medical needle assembly has unique features and capabilities: a removable at will needle hub, which not only allows the surgeon to use the epidural/spinal needle initially to access the epidural or subarachnoid space of the spinal cord; but also permits the surgeon to use the same medical needle assembly again as a tunneling instrument. This allows the surgeon to perform the process of subcutaneous tunneling safely and in a manner previously considered to be surgically improbable.

5 Claims, 10 Drawing Sheets

Fig. 1 (Prior Art)

Brief Overview of the Implant Procedure for a Neurostimulation System*

[1] Prepare the patient using fluoroscopy to identify the appropriate vertebral intervals. Mark those intervals on the patient's skin.

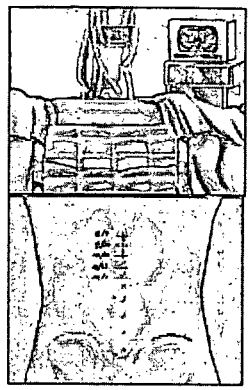

[2] Use a local anesthetic so the patient is alert and able to respond during the procedure. Then, insert a needle at the spinal location appropriate for the patient. Confirm the needle placement using fluoroscopy.

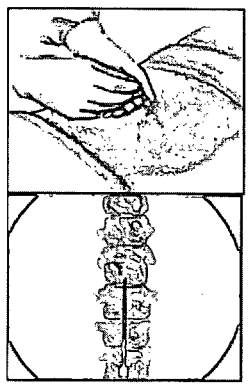

[3] Introduce the lead through the needle and advance the lead tip to the spinal location corresponding with the patient's pain. Confirm lead placement in the epidural space using fluoroscopy. If more than one lead is to be used, repeat steps 2 and 3, placing a second needle for the second lead.

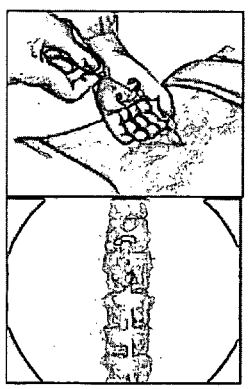

[4] Connect the lead(s) to an external cable and the cable to an external source of power called a screener. Test the effect of stimulation and adjust the

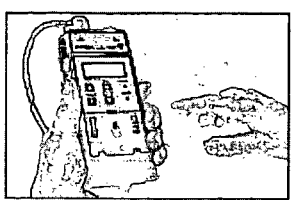

Fig. 1 continued parameters for optimal pain relief. The patient will provide verbal feedback regarding where he or she feels paresthesia (tingling) over the pain area. If neccessary, adjust the lead position(s) for optimal pain relief. When good paresthesia is achieved, anchor the lead(s) in place. The patient uses the screener for several hours up to a few days to test the effectiveness of stimulation on his or her pain.

5 If the patient achieves pain control of >50% during the screening test period, the physician and patient may agree to proceed with the implantation of the system.

If the physician uses a surgically-placed, paddle-type lead(s), proceed with step 6.

If the physician uses the same lead(s) as used during the screening test, proceed to step 8 for the internalization of the neurostimulator.

If the physician uses a percutaneously placed lead(s), but not the one(s) used during the screening test, repeat steps 1-4 to place the lead(s) for the implanted system, then continue with step 8 for the internalization of the neurostimulator. Repeat Steps 1-4; then go to Step 8.

6 Perform the appropriate surgical procedure to expose the dura mater. Introduce a lead blank (same size and shape as the lead, but without electrodes) at a shallow angle to prepare the pathway. Remove the lead blank. Pass the surgical lead

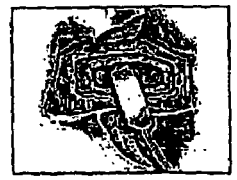

Fig. 1 continued until the entire lead paddle is in the epidural space.

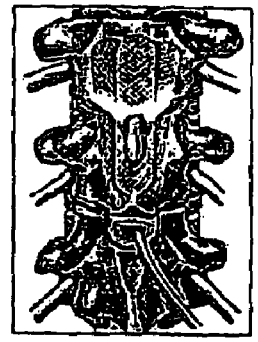

7 When the lead is in place, connect the lead to an external cable, and the cable to the screener. Adjust the lead position for optimal pain coverage (as was done during the screening test, step 4). When testing is complete, disconnect the external cable.

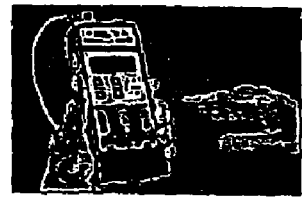

8 Anchor the lead and proceed with the implantation of the neurostimulator. Create a subcutaneous pocket (generally in the patient's abdominal area) for the neurostimulator.

9 Create a tunnel for the extension. Pass the extension through the tunnel and connect to the lead. Next, connect the other end of the extension to the neurostimulator.

10 Use the programmer to communicate with the neurostimulator non-invasively, establish initial parameter settings, and verify system operation.

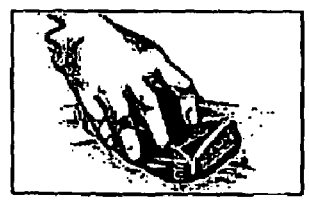

11 Close all incisions and use the programmer to optimize pain control.

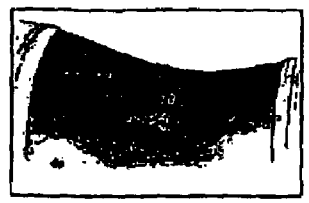

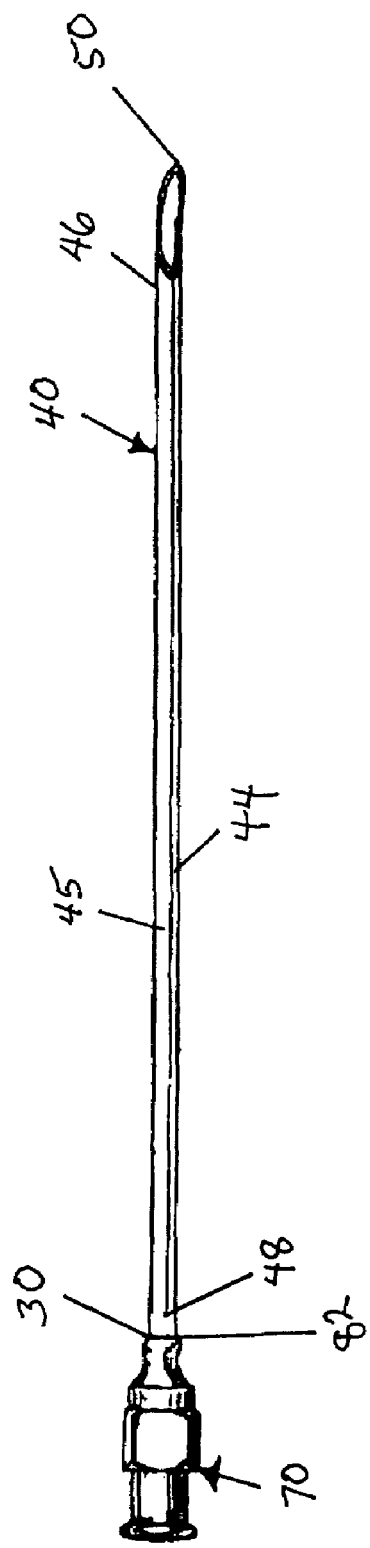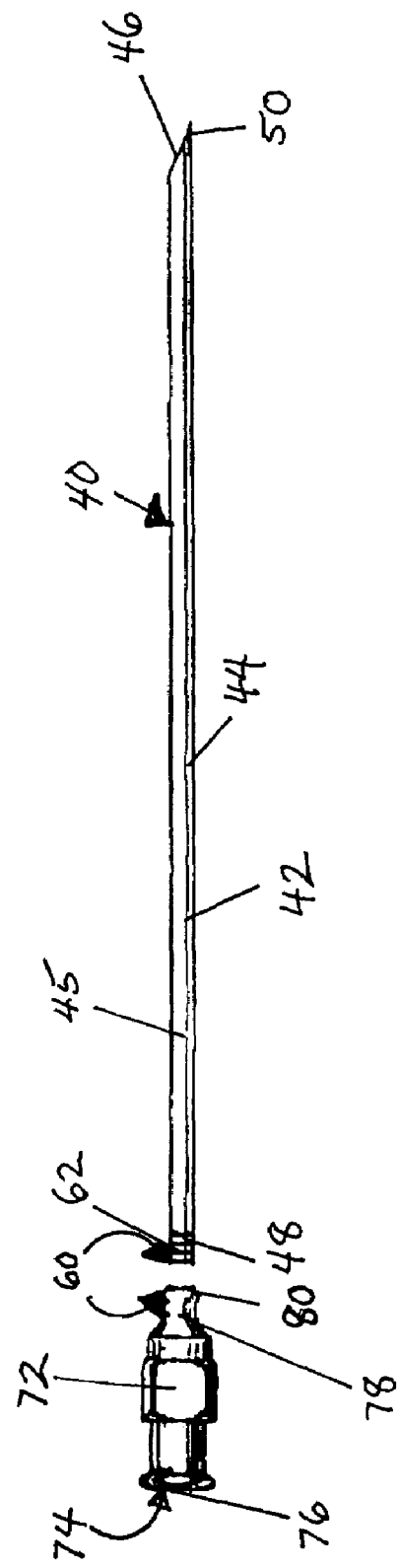

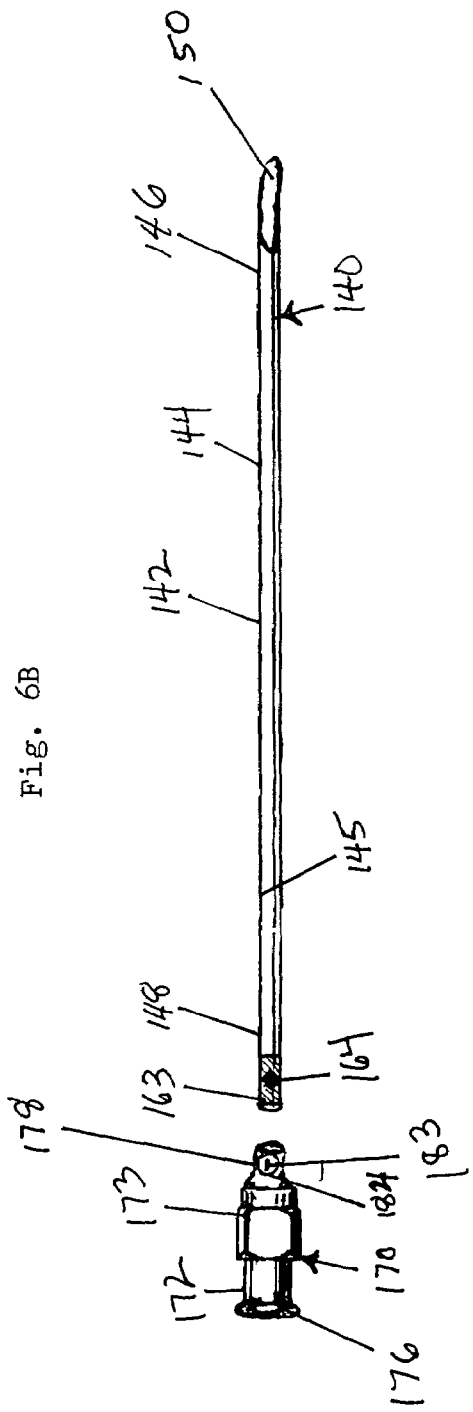
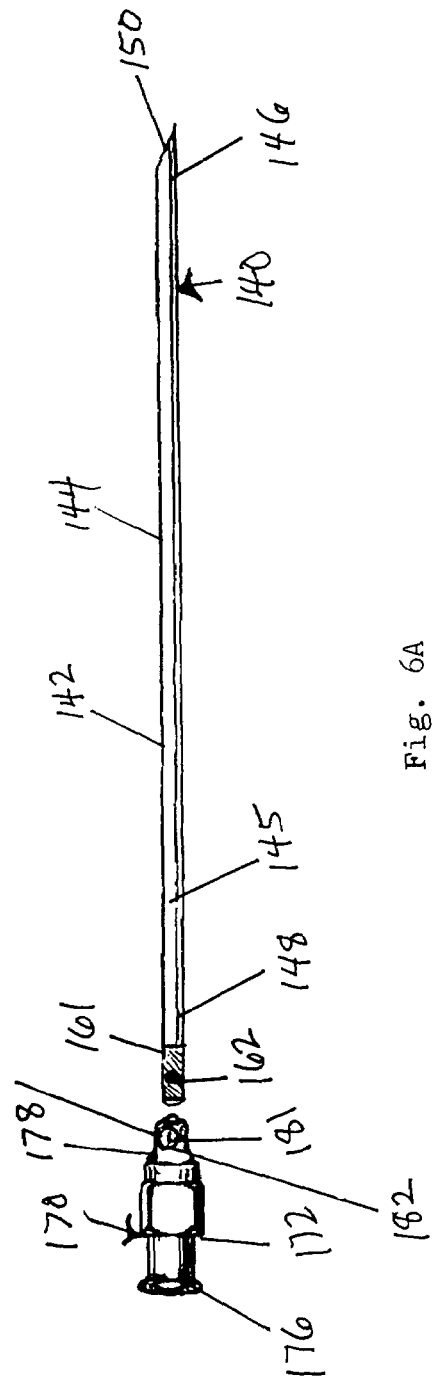
Fig. 6B
Fig. 6A

TUNNELING NEEDLE DESIGN HAVING AN ON-DEMAND REMOVABLE HUB

FIELD OF THE INVENTION

The present invention is concerned with surgical instruments employed for percutaneous tunneling from a surgical entry site on the skin which accesses the epidural and/or subarachnoid spaces surrounding the human spinal cord. It is particularly directed to the creation and use of a modified epidural/spinal needle device for safe tunneling through the subcutaneous tissues to externalize a temporary catheter or spinal cord stimulator lead at a location remote to the original surgical incision.

BACKGROUND OF THE INVENTION

In the field of pain management and neurosurgery, certain surgical procedures often require the internal placement and passage of tubes or wires from the spine to an external drainage system, a drug infusion system, or an electrical power source. Passage is best made through a subcutaneous tunnel in order to reduce the possibility of local or generalized infection; as well as to provide a secure anchor to the skin in order to avoid dislodgement of the electrical wire lead, surgical drain, or any other elongated tangible entity.

Some representative procedures which routinely require tunneling for the subcutaneous placement of a device from the primary incision site are exemplified by and include the following:

(i) Short-term epidural or subarachnoid infusions of opioid drugs. These procedures are frequently performed in order to improve the quality of life for patients with terminal cancer or for patients with nonmalignant pain who require a "trial" (e.g., a temporary infusion) of such medications to determine eligibility for implantation of a permanent drug delivery pump.

(ii) The "trial" (i.e., temporary) infusions of intrathecal Lioresal (or other skeletal muscle relaxants) for control of severe spasticity.

(iii) The placement of a lumbar drainage tube to facilitate chronic closed CSF drainage. This is frequently used in neurosurgery to reduce intracranial pressure, and for the emergency or temporary relief of hydrocephalus. Complications such as infection, catheter kinking, and leakage of CSF around the tube may be obviated by a subcutaneous tunnel through which a segment of the catheter passes to an exit site.

(iv) When performing a spinal cord stimulator "trial", subcutaneous tunneling and placement of electrical lead wires from the spinal incision to an external electrical power source may reduce the risks of infection and dislodgment. Spinal cord stimulators are often implanted in patients with chronic neuropathic pain.

Conventional Subcutaneous Tunneling Procedures

Today, the standard medical practice and conventionally accepted technique for subcutaenous tunneling from an open incision (which accesses either the epidural or subarachnoid space of the spine) is first, to choose an exit site remote from the surgical incision. The tunneling device (typically, a Tuohy epidural needle) is placed from the exit site towards the surgical incision. The sharp open tip end of the Tuohy needle is driven towards the incision. The catheter or wire is then placed through the sharp tip of the needle via the hollow shaft until it passes through the hub into the ambient environment.

At this moment, the tunneling process and effect has been substantively achieved. The distal end of the discrete catheter, drain or wire lead is now visible to the eye and appears externally exposed to the ambient environment from the void center of the needle's hub, at the exit site on the patient's skin.

In order to complete the surgical procedure properly, the surgeon then physically grasps the needle's hub by hand; and pulls the needle shaft and hub out of the exit site using hand force, at which point the needle is removed and the tunneling process is complete.

Clearly, therefore, the overall result of this surgical tunneling technique is: The proximal portion of the discrete catheter, drain, or wire lead remains within the spine and the surgical incision site; the axial length of the catheter, drain, or wire lead lies intact and unimpeded within the newly generated subcutaneous tunnel; and the distal end portion of the catheter, drain or wire lead is externally exposed on the patient's skin at the exit site for subsequent use and manipulation by the surgeon.

To appreciate better the need for and use of the conventional tunneling technique described above, a flow scheme and series of surgical steps when performing a spinal cord stimulator "trial" for a short period of time is presented by Prior Art FIG. 1. As is indicated by Step 9 of Prior Art FIG. 1, a subcutaneous tunnel must be created to house those electrical lead wires that travel away from the implantation site in the spine to a laterally disposed exit site; and the ends of the electrical lead wires must then lie externally exposed at the adjacent location for subsequent attachment to an electrical power source. Clearly therefore, the creation of a subcutaneous tunnel is a vital and necessary part of the surgical procedure.

The focus and purpose of the present invention thus speaks to the mode and manner by which a subcutaneous tunnel is intentionally created to meet and satisfy these surgical demands and procedures. For these reasons also, some degree of knowledge and familiarity with the structure and design of conventionally known and used epidural/spinal needles is necessary and useful.

A Summary Review Of Conventionally Known Spinal And Epidural Needle Designs

A number of scientific and commercial printed publications are known in the pertinent literature which present historical overviews of the pioneers in spinal and epidural needle design. A representative listing includes the following: Frolich, M. A. & D. Canton, "Pioneers In Epidural Needle Design", *Anesth. Analg.* 93:215-220 (2001); Angle et al., "Dural Tissue Trauma And Cerebrospinal Fluid Leak After Epidural Needle Puncture: Effect Of Needle Design, Angle, And Bevel Orientation", *Anesthesiology* 99: 1376-1382 (2003); Chandola et al., "Combined Spinal-Epidural Anaesthesia Techniques . . . A Review", *Indian J. Anaesth.* 49(6): 450-458 (2005); as well as the references cited internally within these publications. Each of these printed publications are expressly incorporated by reference herein.

Also for the reader's benefit, a condensed summary of spinal and epidural needle design is presented below, and is illustrated in part by Prior Art FIG. 2.

For all meaningful purposes, the modern use of spinal anesthesia began in 1931, when a Romanian obstetrician Eugene Aburel [E. Aburel, *Bull. Soc. Obstet. Gynecol. Paris* 20:35-39 (1931)] injected chinocaine through a silk ureteral catheter to block the lumboaortic plexus of laboring women. Aburel is now reoganized not only for using a lumbosacral approach, but also for suggesting a method for obtaining a continuous peridural (epidural) block. However, most medical historians date the regular use of epidural anesthesia from a 1933 article [A. M. Dogliotti, *Am. J. Surg.* 20:107-118 (1933)] authored by an Italian surgeon, Archile Mario Dogliotti, who performed abdominal surgery with single-shot lumbar epidural anesthesia and popularized the idea.

Later, Hingson and Edwards [Hingson, R. A. & W. B. Edwards, *Curr. Res. Anesth. Analg.* 21:301-311 (1942)] showed the potential of continuous epidural anesthesia while working at a Staten Island hospital during World War II. They devised a method for continuous caudal anesthesia and used it on 33 laboring patients in 1942. For this purpose, Hingson and Edwards adapted an earlier method first developed for continuous spinal anesthesia by W. T. Lemmon [W. T. Lemmon, *Ann. Surg.* 111:141-144 (1940)].

Hingson subsequently published a second paper in collaboration with the surgeon James Southworth [R. A. Hingson and J. L. Southworth, *Curr. Res. Anesth. Analg.* 23:215-217 (1944)]. This 1944 paper described a lumbar approach for continuous epidural anesthesiai in which Hingson did not use a malleable needle (as he had for laboring women); but used instead a "large," (presumably a 15-gauge) Barker spinal needle [illustrated by Prior Art FIG. 2A] and a silk ureteral catheter advanced to "but not into the peridural space". This technique was essentially the same approach that Aburel had tried several years before, but this effort was far less successful than the first. Hingson and Southworth obtained satisfactory anesthesia in only 10 of 16 patients; and the placing of the sharp pointed needle in the epidural space, not to mention maintaining the position of the catheter, must have been a major challenge in and of itself.

The Tuohy Needle Design

Edward B. Tuohy was an enthusiastic advocate of neuraxial blockade and was interested in continuous spinal anesthesia. Procedurally, he initially used a 15-gauge Barker needle and a No. 4 silk catheter rather than Lemmon's malleable needle [see E. B. Tuohy, *Anesthesiology* 5:142-148 (1944)].

Subsequently however, Tuohy made a major design change when he replaced the sharp Barker needle with a needle structure that had been designed by Ralph L. Huber [see Prior Art FIG. 2B]. Huber's needle had a directional tip, which allowed anesthesiologists to direct the catheter as it exited the needle tip. The long, sharp, curved tip of the Huber Point epidural needle was designed to lessen the pain of an injection and decrease the risk of depositing plugs of skin into underlying tissues [see U.S. Pat. No. 2,409,979 for details].

However, it was Tuohy himself that recognized that the directional point of the Huber needle might facilitate placement of spinal catheters [E. B. Tuohy, *Anesthesiology* 5:142-148 (1944)]. As a further improvement, Tuohy also added a stylet to the needle design, thereby further decreasing the risk of skin plugging. These marked changes and improvements have caused the combined Tuohy-Huber needle design to become popularly known as the "Tuohy needle".

Subsequently, a number of other physicians also made other changes and modifications to the needle design based on the "Tuohy needle" structure, but not all of these other changes were advantageous.

For example, Charles E. Flowers was probably the first to alter the Tuohy-Huber needle by blunting the bevel and designing the stylet to protrude past the needle tip. Flowers reasoned that the blunt tip would further reduce the risk of dural puncture. He also thought that the sharp protruding stylet would make it easier to pierce the skin. This design approach did not work. However, the resulting Touhy-Flowers needle design [see Prior Art FIG. 2C] tended to bend at the tip, making it difficult, if not impossible, to remove the stylet or to thread the catheter.

Robert Hustead also made his own modifications to the Tuohy-Huber needle design. Hustead sanded off the sharp tip of the original Tuohy/Huber needle, thereby eliminating the secondary bevel of the original needle tip; and also changed the angle of the bevel. The outcome was the Hustead needle design [see Prior Art FIG. 2D] which has a needle opening not exceeding 2.7 mm in length, with an angle for the needle bevel of 12°-15°. In addition, Hustead smoothed the heel of the needle bevel to reduce the danger of trapping and cutting the tubing, should it have to be withdrawn [Monojet, product data sheetPD-222, Sherwood Medical, 1974].

The Weiss Needle Design

Another major needle design change occurred in 1961 when Jesse Weiss dulled the needle tip and added "wings" to the original Tuohy/Huber needle [see Prior Art FIG. 2E] in order to make it easier to grasp the needle with both hands for placement. This modified needle hub design is preferred by many anesthesiologists who use the "loss-of resistance" technique to identify the epidural space in-vivo. However, for Weiss himself (who practiced the "hanging drop" method to identify the epidural space in-vivo), the addition of wings to the needle design was crucial because it allowed him to slowly advance the needle with both hands while observing the fluid drop disappearing as the tip of the needle entered the epidural space.

The Sprotte Spezial Needle Design

Jurgen Sprotte made several significant design contributions in needle design. In 1979, Sprotte developed a pencilpoint needle for spinal anesthesia, which has a noticeable difference in its needle tip geometry [see Prior Art FIG. 2F]. Thus, while the previous spinal needle design had a short, cylindrical-tip configuration, Sprotte substituted and used a olive-shaped, rounded-tip geometry. Sprotte believed that this modification would minimize tissue damage because his spinal needle design would spread rather than cut tissue fibers in-vivo.

Then in 1987, Sprotte made his needle modifications more suitable for epidural use. He added a special plastic wedge to the inside of the needle tip that would direct an epidural catheter toward the lateral needle hole. Although it uses a different needle-tip geometry, this Sprotte Spezial needle has the very blunt tip shared with the original Crawford, Hustead, and Weiss needle designs.

The Crawford Needle Design

O. B. Crawford was an anesthesiologist who preferred a needle with a straight tip. For this purpose, Crawford developed a Quincke-type epidural needle with an extremely short, and thus a very blunt, bevel tip [see Prior Art FIG. 2G]. The bevel of this needle was very flat (60° if measured from the longitudinal axis of the needle); and Crawford used it to identify the epidural space with the needle bevel turned down. Also when the Crawford epidural needle was inserted in the high thoracic area with a cephalad direction approximately 60° from the patient's back, the opening of the needle would be parallel to the longitudinal ligaments, and thus was very unlikely to perforate the dura. After the epidural space was identified, he rotated the bevel of the needle 180°, which brought the needle bevel into a position wherein the catheter would be likely to exit with a cephalad direction.

Alternative Epidural Needle Designs

Many other styles of epidural needles have also been designed. For a number of different reasons, these alternative formats have received less attention in the technical field, but should be briefly mentioned herein. Among these alternatives are: the Wagner needle (1957); the Cheng needle (1958); the Crawley needle (1968); the Foldes needle (1973); and the Bell needle (1975)—all of which are variants of the Huber needle design [see Prior Art FIG. 2B] and have a blunted tip of varying sharpness.

Of these alternative needle structures, the Cheng design [see U.S. Pat. No. 2,922,420] is most remarkable, because it was the first epidural needle with centimeter markings to indicate depth [P. A. Cheng, *Anesthesiology* 19:556-559 (1958)]. Unfortunately, the Cheng needle was described as "cumbersome" to use and "extremely difficult to effect" by Cheng's contemporaries; and like many other needle designs, it is not commercially available for use today.

In addition to these, there is the Brace needle, a Crawford design variant; the Lutz epidural needle (1963), with a pencil-point design for single-shot epidural use; the Scott needle (1985), a Tuohy needle design with a Luer lock hub; and the Eldor needle (1993), each designed for use with combined spinal epidural anesthesia.

Refinements Which Transcend The Different Needle Designs

In recent years, a wide range and variety of format changes have been proposed for existing designs of epidural/spinal needles. A representative listing of such format changes is presented below.

(i) Spinal needles in which the sharp end tip has a reduced diameter in comparison to the diameter of the needle body. See for example U.S. Pat. Nos. 3,216,616; 3,388,703; 3,540,447; 4,335,718; 4,781,691; and 4,909,800.

(ii) The presence of multiple holes or apertures in the insertion tip end of a spinal needle. See for example U.S. Pat. No. 5,848,996.

(iii) The existence of multiple lumens in epidural/spinal needles. See for example U.S. Pat. Nos. 4,808,157; 4,958,901; and 5,163,901.

(iv) Spinal needles having a curved or flared distal end. See for example U.S. Pat. Nos. 4,889,529; 5,628,734; 5,669,882; 6,565,542; and 7,070,596.

(iv) The use of multiple needles, where a small diameter needle unit is introduced through the lumen of a larger diameter needle unit. See for example U.S. Pat. Nos. 3,780,773; 4,917,670; and 4,994,036.

The Long-Standing Problems

Despite all these innovations and developments in spinal needle design, there remains a well recognized problem and long-standing potential danger when conventional spinal needles are employed as devices for subcutaneous tunneling.

As has described previously herein, the standard needle tunneling procedure begins at a secondary external exit site on the skin which is remote from the primary surgical incision site. The sharp open tip end of the tunneling needle is passed under the skin towards the primary surgical incision. The use of this technique introduces a serious risk of cutting or severing the catheter or wire when the sharp tip is pushed into the incision where the catheter or wire is located. Additionally, the tunneling of the needle from the exit site towards the surgical incision increases the possibility of bacterial contamination since the needle is being introduced through potentially colonized skin at the remote exit site.

Clearly therefore, it would be most desirable for the surgeon to employ a needle at the primary incision site whose design allows it to be used also as a tunneling instrument, and which would avoid these different kinds of unfortunate problems, limitations and medical complications. The generation of such a design structure would be recognized and appreciated by surgeons and physicians alike as a unique innovation and unforeseen improvement having singular medical benefits and surgical advantages.

SUMMARY OF THE INVENTION

The present invention is directed to a needle design, a method of use, and a system to reduce the risks of infection and damage to catheters or leads associated with the implantation of drug pump trials or spinal cord stimulators trial leads. This is achieved by attaching a removable hub to the needle tunneling device.

This simplified needle design thus eliminates the need to use a separate device for tunneling.

Furthermore, the presence of a removable hub not only facilitates safe and easy tunneling, but also provides an entirely new procedure for subcutaneous tunneling. In this new technique, the conventionally known tunneling process is reversed and will start by placing the needle at the surgical incision site with the short tip pointed away towards the desired exit point on the skin. The needle will then be pushed through the subcutaneous tissues and will subsequently pierce the skin at the desired exit point. Once this is accomplished, the stylet is removed, and the hub is unscrewed from the blunt end of the needle, thus allowing a catheter or wire to be passed through the hollow shaft of the needle towards the needle tip. After the catheter or wire exits the tip of the needle, the clinician will hold the catheter in the incision space with one hand and with the other hand will safely pull the needle out through the exit site leaving the catheter safely tunneled.

The invention as a whole provides several important advantages.

1. By directing the needle from the surgical incision site to the exit site the possibility of introducing bacteria is minimized.

2. The possibility of damaging the catheter or wire leads with the sharp end of the needle as it emerges into the surgical incision space is markedly reduced.

3. This safe needle has a double function : the needle can be used to pierce the desired tissue surface; and, in addition, the needle can also be used as a tunneling device, eliminating the need for an additional tunneling instrument. Cost is reduced.

4. The use of a needle for a short tunneling distance (typically less than 15 cm), obviates the need to create a rather large initial surgical incision, which is typically required when a separate tunneling instrument is to be used.

All these desirable features and advantages will be recognized by the detailed description that follows.

BRIEF DESCRIPTION OF THE DRAWING

The present invention may be more easily understood and better appreciated when taken in conjunction with the accompanying Drawing, in which:

Prior Art FIG. 1 is a flow scheme and series of conventional surgical steps for performing a spinal cord stimulator "trial" over a short period of time, in accordance with good medical practices;

Prior Art

FIGS. 4A and 4B illustrate a preferred embodiment of the needle body and needle hub in the medical needle assembly shown by FIGS. 3A and 3B;

FIGS. 6A and 6B illustrate a first alternative embodiment of the needle-hub construct for the present invention;

DETAILED DESCRIPTION OF THE INVENTION

The present invention is in part a unique medical needle assembly which provides a removable on-demand needle hub for a spinal needle suitable for accessing the epidural or subarachnoid space of the spinal cord. This improvement in spinal needle design allows and facilitates the purposeful tunneling of a tangible object having an extended linear length (such as a catheter, or drain, or electrical wire lead of about 15 cm size or less) as well as the capability to externalize the distal end of the object at an anatomic location remote to the original surgical incision site.

The singular feature of a medical needle assembly which has a removable on-demand needle hub has distinct and unforeseen benefits. Among them are the following:

This improved needle design not only allows the surgeon to use the assembled spinal needle to access the epidural or subarachnoid space of the spine in accordance with standard good medical practices; but also permits the surgeon to use the same needle assembly as a safe tunneling instrument when performing the adjunct process of subcutaneous tunneling, in a manner and method previously considered to be surgically improbable.

It will be appreciated also that the innovative tunneling method provided by the present invention comprises a series of manipulative steps which are counter-intuitive in orientation and are contrary to conventional tunneling direction. This is due in part to the fact that the tunneling effort begins from the pre-existing primary surgical incision site (the access to the epidural or subarachnoid space) and then travels away laterally towards the pre-chosen remote exit location—a direction and orientation which lies in opposition and contradiction to the convention standard medical practice, which starts the tunneling at the remote anatomic exit location and continues onward towards the pre-existing primary surgical incision site. This reversal of convention medical practice and standard surgical tunneling procedure markedly reduces the risk of damage typically caused by the sharp end tip of the tunneling needle to the implanted catheter, or drain, or electrical wire lead within the open channel of the primary incision site.

I. Multiple Embodiments Of the Medical Needle Assembly

The instant invention provides an assembled medical needle which is suitable for use both as a spinal needle to access to the epidural or subarachnoid space of the spine, and as a safety-enhanced tunneling instrument whose design facilitates the placement of a catheter, or drain, or electrical wire lead subcutaneously within a purposefully created tunnel. A range of different embodiments of the medical needle assembly can be prepared to meet the needs or convenience of the surgeon.

A. One Preferred Embodiment

Figure 5:
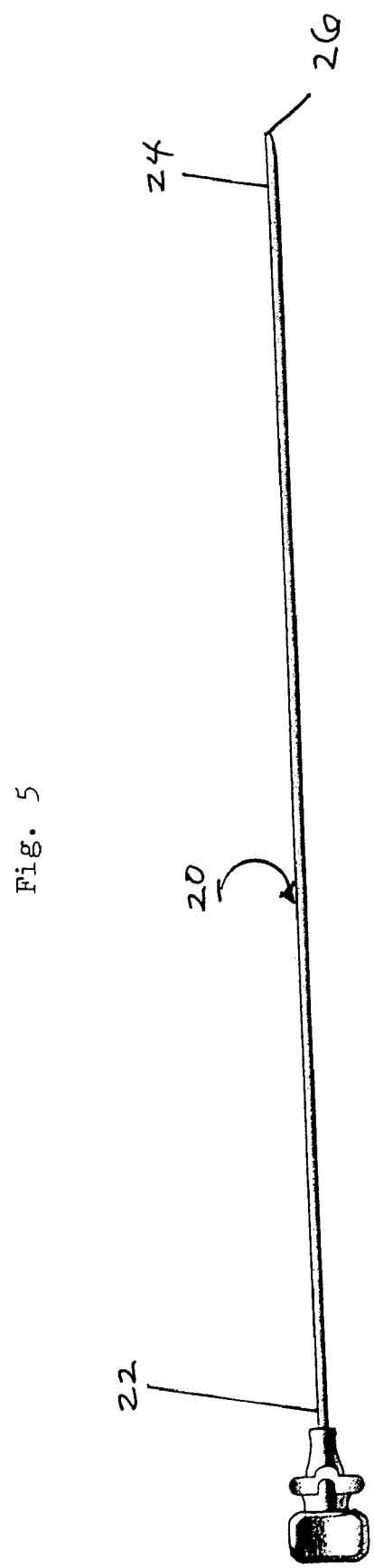
FIG. 5 illustrates a preferred embodiment of a fitted stylet in the medical needle assembly shown by FIGS. 3A and 3B.

A highly preferred embodiment of the improved medical needle assembly is illustrated by FIGS. 3-5 respectively.

Figure 2A:
FIGS. 2A-2G are individual illustrations showing seven different and distinct epidural needle designs conventionally known in the pertinent art.
Figure 2B:
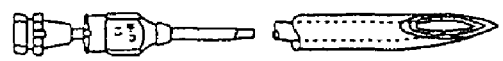
Figure 2C:
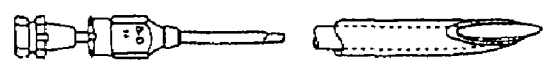
Figure 2D:
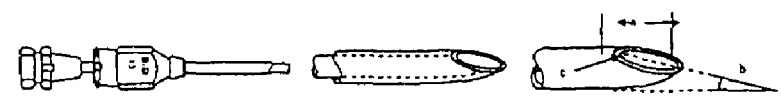
Figure 2E:
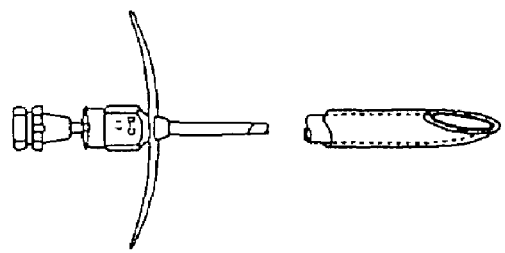
Figure 2F:
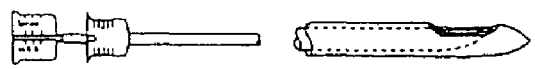
Figure 2G:
Figure 3C:
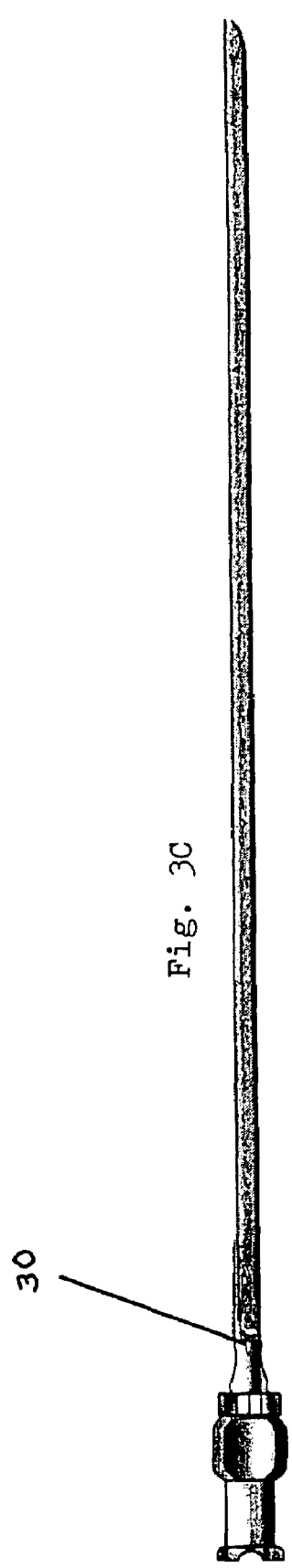
FIGS. 3A-3C illustrate the component parts of the medical needle assembly as a preferred embodiment of the present invention.
Figure 3B:
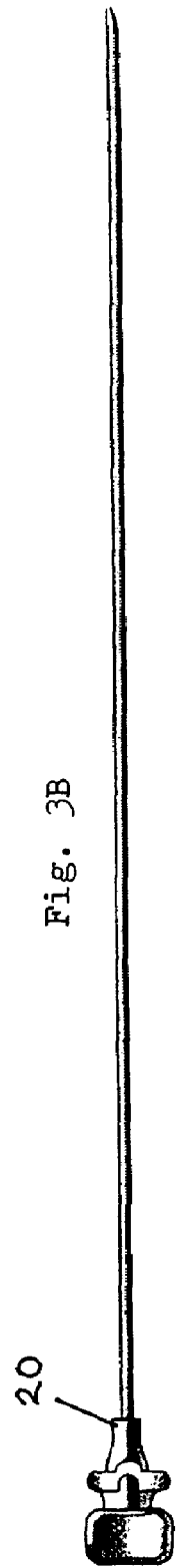
Figure 3A:
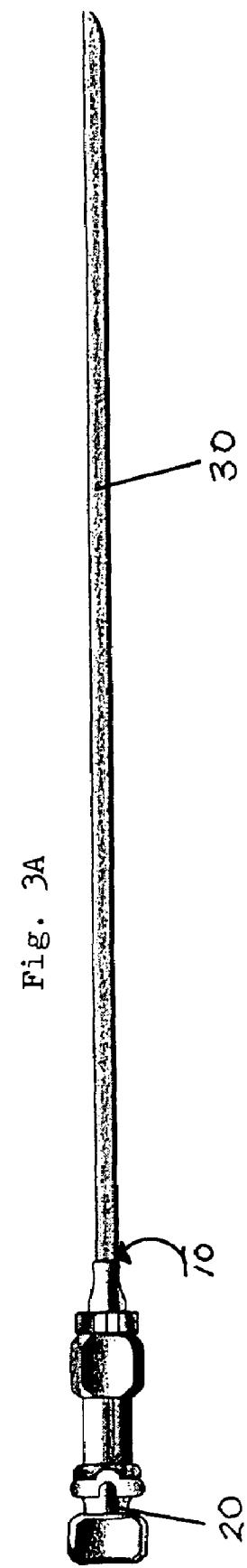

As shown by FIGS. 3A, 3B, and 3C respectively, the complete medical needle assembly 10 comprises a fitted stylet 20 and a needle-hub construct 30. When removed from the assembly 10 and when disassembled, the two requisite component parts forming the needle-hub construct 30 are illustrated by FIGS. 4A and 4B respectively. Similarly, when removed from the assembly 10, the fitted stylet 20 appears as a discrete article as shown by FIG. 5.

The Needle-Hub Construct

As seen in FIGS. 4A and 4B, the needle-hub construct 30 includes an elongated, rigid needle body 40 comprised of: a hollow shaft 42 having fixed dimensions and configuration; at least one solid wall 44 formed of a stiff and unbendable material; an open internal cavity 45 (not shown); and discrete first and second open ends 46, 48.

A sharp open tip 50 is formed at and extends from the first open (distal) end 46. This sharp open tip 50 is employed for cutting through the living tissues in a living subject. The open tip 50 provides an aperture which is in direct flow communication with the open internal cavity 45 and the void volume at the second open (proximal) end 48. In the preferred embodiment, the sharp open tip is also intentionally beveled to facilitate its insertion through the skin and subcutaneous tissues of the living subject.

In addition, discrete engagement means 60 are disposed at and joined to the second open (proximal) end 48 for at will engagement and disengagement of a needle hub 70. A preferred and distinct type of engagement means 60 is shown by FIG. 5B; and constitutes a plurality of aligned screw threads 62, which are disposed over and around the external surface of the elongated needle body 40 at second open end 48. The generation and placement of aligned screw threads in this manner is a conventionally known and easily performed manufacturing technique.

The needle-hub construct 30 also includes a removable on-demand needle hub 70 which has a centrally placed void volume for freely flowing fluid communication. The needle hub 70 is comprised of: a preformed hub structure 72 having preset dimensions and configuration; has at least one solid wall 73 formed of a rigid material; at least one open lumen 74 having a spatial void volume and an internal lumen surface 75 (not shown); and at least two discrete open hub ends 76, 78. Also, attachment means 80 lie disposed at the open end 78 of the hub structure 72 for on-demand attachment and detachment of the needle hub 70 to the second open end 48 of the needle body 40.

In the preferred embodiment shown, the preformed hub structure 72 offers and provides a female luer-lock mechanism (conventionally known in the pertinent art), which allows a standard syringe apparatus to be attached fluid-tight to the needle hub. This preferred female luer-lock format permits the medical needle assembly 10 to be used for injection of liquid preparations and/or the aspiration of fluid from the tissues of the living subject.

In addition, in the preferred embodiment shown, the attachment means 80 desirably take form as a set of corresponding screw threads 82 which are disposed over and around the internal lumen surface 75 at the open end 78 of said hub structure 72. The set of screw threads 82 are of a diameter and depth size to correspond precisely with and fully engage the aligned screw threads 62 (the preferred engagement means) disposed on the external surface of the elongated needle body 40 at the second open end 48. Accordingly, the set of corresponding screw threads 82 constitute and embody a preferred means for achieving on-demand attachment and detachment of the needle hub 70 to the second open end 48 of the needle body 40.

The Fitted Stylet

The details of the fitted stylet 20 are shown by FIG. 5 and are conventionally known. As seen therein, the stylet 20 has a proximal end 22, a stylet body 24, and a distal end 26. Moreover, the stylet 20 is dimensioned and configured to pass freely through the internal void volume provided by both the needle hub 70 and the needle body 40; and to rest indefinitely within the interior spatial volume provided by the hub's internal lumen 74 and the open internal cavity 45 of the needle body 40.

The fitted stylet 20 may be withdrawn and inserted repeatedly as needed or desired from the needle-hub construct. The length and overall dimensions of the fitted stylet are sufficient to occlude the internal void volume of the needle-hub construct 30 whenever the stylet is inserted.

Some Attributes of the Preferred Embodiment

The preferred medical needle device will demonstrate the following attributes:

It is formed of stainless steel;

It has a length typically varying between 10 and 15 cm;

It is desirably of a gauge varying between 15 and 17;

It has a directional tip and fitted stylet to decrease the risks of skin plugging; and It presents a 180 degree rotation luer lock at the intersection of the hub with the proximal end of the needle shaft.

B. Alternative Modes Of Connection And Disconnection

It will be noted and appreciated that many different and diverse modes and manners for connecting and disconnecting the needle body to the needle hub can be prepared. These different modes and manners of juncture on-demand are typically structural forms of linkage, are frequently employed in assemblies and arrays, and are conventionally used and well established devices within the mechanical arts.

Thus, while the present medical needle instrument can be prepared in a variety of alternative embodiments, these alternatives, however, differ substantively only in the structural design and format of two features: (1) the engagement means disposed at the second open end of the needle body for at will engagement and disengagement of a needle hub; and (2) the attachment means disposed at one open end of the hub structure for on-demand attachment and detachment of the needle hub to the second open end of the needle body. In short, the differences meaningfully lie in the mechanisms used to connect and disconnect the hub structure to and from the needle body, when and as desired.

Accordingly, merely to demonstrate the range and variety of the many different and diverse modes and manners for connecting and disconnecting the needle body to the needle hub, two exemplary alternative embodiments are presented below. It will be expressly noted and understood, however, that these two alternative formats are only representative of the full range and variety of on-demand juncture formats that can be employed; and that the particular means for juncture described by the alternative embodiments is neither limiting nor restrictive of the true range and variety of available choices.

A First Alternative Embodiment

In this first alternative embodiment, only the engagement means disposed at the second open end of the needle body, and the attachment means disposed at one open end of the hub structure differ from those in the preferred embodiment described above. This first alternative embodiment is illustrated by FIGS. 6A and 6B.

Thus, as shown by FIGS. 6A and 6B, the needle-hub construct 130 includes an elongated, rigid needle body 140 comprised of: a hollow shaft 142 having fixed dimensions and configuration; at least one solid wall 144 formed of a stiff and unbendable material; an open internal cavity 145; and discrete first and second open ends 146, 148.

A sharp open tip 150 is formed at and extends from the first open end 146. In addition, discrete engagement means 160 are disposed at and joined to the second open end 148 for at will engagement and disengagement of a needle hub 170.

The particulars of the engagements means 160 in this first alternative embodiment comprise rectangularly shaped friction plates 161, 163 which formed of a resilient and inflexible material. The friction plates 161, 163 are disposed in opposite parallel position and alignment upon the external surface of the needle body 140 and lie adjacent to the second open end 148. Also, within each friction plate 161,163 is a substantially circular recess or depression 162, 164, which does not penetrate or pierce the solid wall 144 of the needle body 140.

The two friction plates and their circular recesses can be prepared as individual and discrete items and then subsequently permanently joined (via adhesives, welding, sonic bonding, etc.) to the solid wall of the needle body adjacent to the second open end; or, if desired, the friction plates and circular recesses can be integrated and incorporated into the solid wall of the needle body as a part of an original equipment manufacture.

The needle-hub construct 130 also includes a removable on-demand needle hub 170 which has a centrally placed void volume for free flowing fluid communication. The needle hub 170 is comprised of: a preformed hub structure 172 having preset dimensions and configuration; has at least one solid wall 173 formed of a rigid material; at least one open lumen 174 having a spatial void volume and an internal lumen surface 175(not shown);

and at least two discrete open hub ends 176, 178. Also, attachment means 180 lie disposed at the open end 178 of the hub structure 172 for on-demand attachment and detachment of the needle hub 170 to the second open end 148 of the needle body 140.

The particulars of the attachment means 180 for the first alternative embodiment comprise two small diameter, threaded screw bolts 181, 183, each of which is fitted into a prepared small diameter bore hole 182, 184 on the hub structure 172. It will be noted that each small bore hole 182, 184 is individually disposed in opposite parallel position and alignment on the hub structure 172 at the open end 178; and that each fitted threaded screw is slightly longer in linear length than the depth of the bore hole (and the thickness of the solid wall) in the hub structure; and that each screw bolt can be rotated in either a clockwise or counter-clockwise direction within its individual bore hole in order to extend or withdraw the length of the bolt through its bore hole.

The manner for on-demand connection and disconnection of the needle body 140 to the needle hub 170 is quite simple and proceeds as follows: The second open end 148 of the needle body 140 is inserted into the spatial void volume of the open lumen 174 such that each friction plate 161, 163 is placed in opposite parallel position and in alignment with an adjacently positioned bore hole 182, 184, which contains a fitted threaded screw bolt 181, 183 therein. When proper alignment is achieved, each threaded screw bolt 181, 183 in its bore hole 182, 184 will lie directly over and be able to engage a circular recess 162, 164 in the friction plates 161, 163.

Then, by extending each threaded screw bolt individually within its bore hole, direct contact and friction force will be generated and maintained upon each circular recess in the friction plates. Each threaded screw bolt may be further extended or retracted as needed to maintain sufficient friction force on the frictions plates of the needle body such that the needle hub becomes firmly connected to the second open end of the needle body. Once connected in this manner, the juncture between the needle hub and the needle body will continue indefinitely; and the formed needle-hub construct is an integrated instrument ready for use by the surgeon.

At any time thereafter, the juncture and linkage between the needle hub 170 and the needle body 140 may be terminated immediately or on-demand. To disconnect the parts, the user need only turn the threaded screw bolts 181, 183 in a counter-clockwise direction within its individual bore hole 182, 184. This action will cause a retraction of the threaded screw bolts and quickly diminish the degree of friction force exerted at the circular recesses and the friction plates on the needle body. Once the threaded screw bolts are adequately withdrawn into their bore holes, the second open end 148 of the needle body 140 can be separated and removed entirely from the needle hub 170.

A Second Alternative Embodiment

As before, only the engagement means disposed at the second open end of the needle body, and the attachment means disposed at one open end of the hub structure differ from those in the preferred embodiment described above. The second alternative embodiment is illustrated by FIG. 7.

Figure 7:
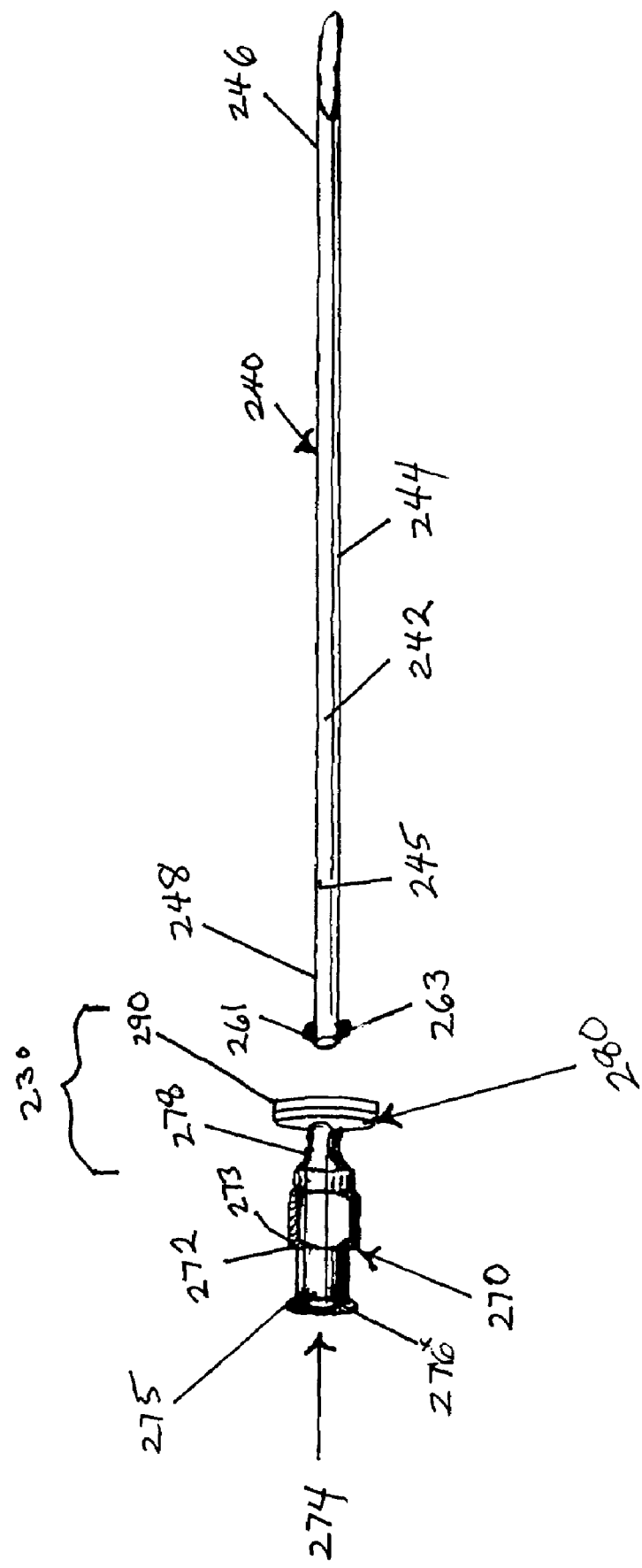
FIG. 7 illustrates a second alternative embodiment of the needle-hub construct for the present invention.

As seen in FIG. 7, the needle-hub construct 230 includes an elongated, rigid needle body 240 comprised of: a hollow shaft 242 having fixed dimensions and configuration; at least one solid wall 244 formed of a stiff and unbendable material; an open internal cavity 245 (not shown); and discrete first and second open ends 246, 248.

A sharp open tip 250 is formed at and extends from the first open end 246. In addition, discrete engagement means 260 are disposed at and joined to the second open end 248 for at will engagement and disengagement of a needle hub 270.

The particulars of the engagements means 260 in this second alternative embodiment comprise two small anchoring nubs or knob-like protuberances 261, 263; which are formed of a resilient and inflexible material and are disposed in opposite parallel position and alignment upon the external surface of the needle body 240 adjacent to the second open end 248.

The two small anchoring nubs 261, 263 can be prepared as individual and discrete items and then subsequently permanently joined (via adhesives, welding, sonic bonding, etc.) to the solid wall of the needle body adjacent to the second open end; or, if desired, the small nubs can be incorporated into the solid wall of the needle body as a part of an original equipment manufacture. In addition, the nubs may be either hollow or completely solid in structure; can be configured as geometrical or irregularly shaped mounds; and may be smooth surfaced or roughly finished. In general, however, the size dimensions of the nubs are desirably in the millimeter of less range, and the overall volume of the nubs should be as small as possible so long as they can serve as anchor points for the needle body.

The needle-hub construct 230 also includes a removable on-demand needle hub 270 which has a centrally placed void volume for free flowing fluid communication. The needle hub 270 is comprised of: a preformed hub structure 272 having preset dimensions and configuration; has at least one solid wall 273 formed of a rigid material; at least one open lumen 274 having a spatial void volume and an internal lumen surface 275; and at least two discrete open hub ends 276, 278. Also, attachment means 280 lie disposed at the open end 278 of the hub structure 272 for on-demand attachment and detachment of the needle hub 270 to the second open end 248 of the needle body 240.

Figure 8B:
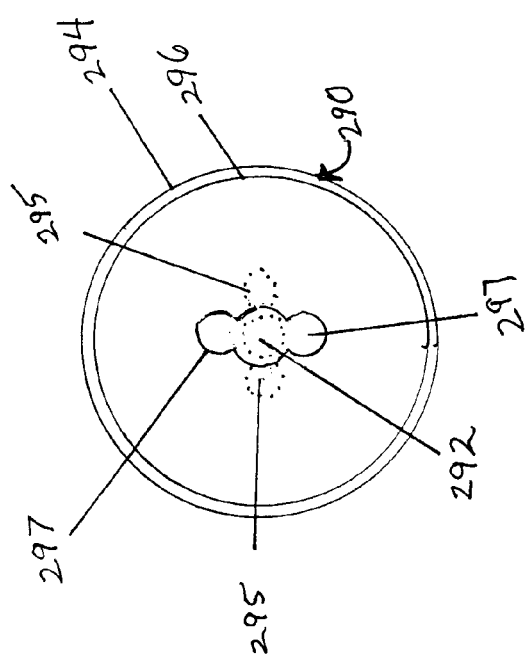
FIGS. 8A and 8B illustrate the details of the at will engagement means and the on-demand attachment means for the second alternative embodiment shown by FIG. 7.
Figure 8A:
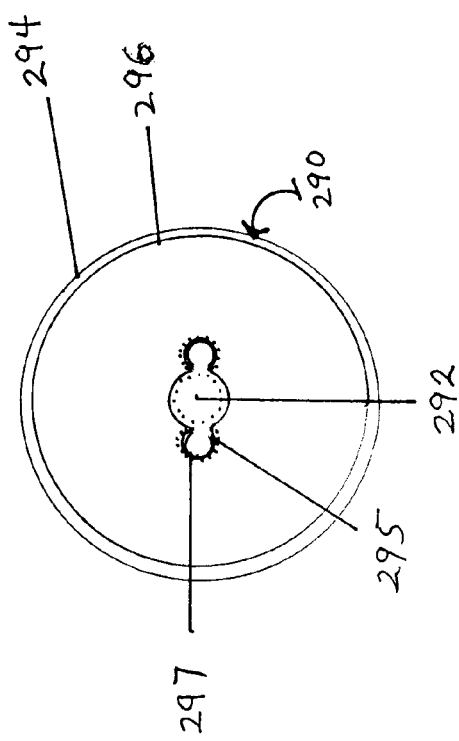

The particulars of the attachment means 280 for the second alternative embodiment comprise a circular clamp 290 which is integrally joined to the spatial void volume of the open lumen 274 at the open end 278 of the hub structure 272; and has a central aperture 292 which is circumscribed, joined to, and shared in common with the internal lumen surface 275, as is seen in FIGS. 7, 8A and 8B. The circular clamp 290 is thus an appendage linked to and extending from the open end 278 of the hub structure 272.

Also, as shown by FIGS. 8A and 8B, the circular clamp 290 is structurally formed by two rounded discs 294, 296 which are linked together. However, the interiorly disposed disc 294 is fixed to the open end 278 of the hub structure 272 in its aligned position, and thus is immobile. In comparison, the externally disposed disc 296 is rotably mounted with respect to its twin; and the disc 296 can be freely turned by hand force whenever it suits the surgeon to do so.

Note also that the interiorly disposed disc 294 and the externally disposed disc 296 are alike in that each disc comprises an oppositely positioned pair of substantially circular cutouts 295, 297 which begin at the central aperture 292, and then extend outwardly for a very short distance (about a millimeter or less) towards the disc perimeter edge. In this respect, it is very desirable that oppositely positioned pair of substantially circular cutouts 295, 297 be identical in size, shape and volume. This is necessary in order that the oppositely positioned pair of circular cutouts 295, 297 be able to receive and accommodate the two small anchoring nubs 261, 263 protruding from the exterior surface of the needle body 240; and when this event occurs, that the discs be able to function as a clamp.

Accordingly, when the two discs 294, 296 are placed in proper orientation to begin the joining of the needle hub 270 to the needle body 240, as illustrated by FIG. 8A, the pair of circular cutouts 295 existing on the fixed disc 294 are placed so they directly overlay and are precisely aligned with the pair of circular cutouts 297 present on the rotable disc 296. This positioning of the discs 294, 296 constitutes the opening of the clamp in a mode ready for receipt of the needle body 240.

The on-demand connection and disconnection of the needle body 240 to the needle hub 270 is then easily performed: The second open end 248 and the two small anchoring nubs 261, 263 extending from the needle body 240 are inserted into the central aperture 292 and the pair of circular cutouts 297 existing on the rotable disc 296 concurrently; and then are pushed further into the central aperture 292 and the pair of circular cutouts 295 existing on the fixed disc 294.

At that moment, the rotable disc 296 can be freely turned (clockwise or counter-clockwise) by hand force; and the rotation of the mobile disc 296 over any radial distance will cause a radial displacement of the circular cutouts 297 such that they no longer overlay nor are aligned with the circular cutouts 295 on the fixed disc 294. Instead, the material substance of the mobile disc 296 now physically blocks and complete obscures the contents of the circular cutouts 295 existing on the fixed disc 294, as illustrated by FIG. 8B—those internalized contents being the second open end 248 and the two small anchoring nubs 261,263 extending from the needle body 240.

Once connected in this manner, the juncture between the needle hub and the needle body can continue indefinitely; and the formed needle-hub construct is an integrated instrument ready for use by the surgeon.

At any time thereafter, the clamp juncture between the needle hub 270 and the needle body 240 may be terminated whenever desired. To cause a disconnection of the parts, the user need only turn the mobile disc 296 back such that the pair of circular cutouts 297 again directly overlay and are precisely aligned with the pair of circular cutouts 295 existing on the fixed disc 294, as shown by FIG. 8A. This action will create open and unhindered access to the second open end 248 and the two small anchoring nubs 261,263 extending from the needle body 240, which can then be removed entirely from the needle hub 270.

II. The Manipulative Steps Comprising The Methodology

The present invention also offers a safe method for placing a tangible object within a purposefully created subcutaneous tunnel, wherein the linear length of the object extends through the tissues of a living subject from an open channel at a pre-existing primary incision site to a pre-chosen secondary external exit site. For purposes of setting forth the specific details of this unique and unforeseen in-vivo technique, three presumptions have been made. These are: (a) There is a primary incision site already in existence, this primary site having an open channel and access to the epidural or subarachnoid spaces of the spinal cord; (b) a discrete article having a known linear length and two distinct ends (such as a catheter, drain or electrical lead wire) has been surgically placed within the open channel of the primary incision site; and (c) a secondary external exit site has been pre-chosen by the surgeon, this secondary incision site being adjacent and anatomically lateral to the primary incision site.

The Initial Sequence Of Steps

Given these preconditions, the initial sequence of steps is as follows:

Step 1: Assemble a medical needle device comprising an elongated needle body including
  (i) a hollow shaft having fixed dimensions and configuration, at least one solid wall, an open internal cavity, and discrete first and second open ends,
  (ii) a sharp open tip formed at said first of the open ends, and
  (iii) engagement means disposed at the second open end for at will engagement and disengagement of a needle hub;
a removable at will needle hub including
  (a) a preformed hub structure having preset dimensions and configuration, at least one solid wall, at least one open lumen, and at least two discrete open hub ends,
  (b) attachment means disposed at one open end of said hub structure for on-demand attachment and detachment of said needle hub to said second open end of said needle body; and
a fitted stylet configured to pass freely through and lie within said open internal cavity of said elongated needle body.

Step 2: Introduce the sharp open tip of the assembled medical needle into the open channel of the pre-existing primary incision site in the living subject.

Step 3: Orient the introduced sharp open tip of the assembled medical needle which lies within the open channel of the pre-existing primary incision site towards the secondary external exit site in the living subject, recognizing that the secondary external exit site has been pre-chosen to lie adjacent and anatomically lateral to the primary incision site.

Step 4: Insert the oriented sharp open tip of the assembled medical needle present into the adjoining subcutaneous tissues of the living subject.

Step 5: Forcibly move the inserted sharp open tip of the assembled medical needle away from the primary incision site through the subcutaneous tissues of the living subject until the pre-chosen secondary external exit site is reached subcutaneously.

Step 6: Using said sharp open tip of said assembled medical needle, pierce upwards through to the skin of the living subject until the sharp open tip perforates the skin and becomes externally exposed to the ambient environment at the pre-chosen secondary external exit site.

After performing these six steps, it will be noted that the in-vivo tunneling process as such is essentially complete. A purposely created tunnel has been subcutaneously within the tissues of the living subject; and the length of the generated tunnel extends subcutaneously from the open channel of the primary incision site to the secondary external exit site on the skin of the patient.

The Followup Sequence Of Steps

The present methodology also intends that a tangible object of known linear length can then be placed within the purposely created subcutaneous tunnel. These additional steps are as follows:

Step 7: At the primary incision site, withdraw and remove the fitted stylet entirely from the medical needle.

Step 8: Detach the removable on-demand needle hub from the needle body then lying subcutaneously within the tissues of the subject such that the second open end (the proximal end) of the elongated needle body becomes visible and directly accessible.

Step 8: Pass one linear end of the tangible object into the now accessible second open end and push the linear end through the spatial void of the internal cavity of the elongated needle body, such that the passed linear end exits from the sharp open tip of the elongated needle body and becomes exposed to the ambient environment at the pre-chosen secondary external exit site; and then Step 9: Retract and completely withdraw the entire elongated needle body from the open channel of the pre-existing primary incision site, whereby the linear length of the long tangible object rests and extends over the distance from the pre-existing primary incision site to the pre-chosen secondary external exit site within the purposefully created subcutaneous tunnel.

Finally, several other considerations are identified when using the present methodology as a medical/surgical procedure:

RISKS: The same as with spinal needles presently manufactured and commercially available. These long recognized medical risks include but are not limited to: bleeding, dural tear (with subsequent headache, dizziness, vertigo, nausea, vomiting, dehydration, double vision), nerve injury, pain at the site of insertion.

CONTRAINDICATIONS: Systemic or local infections, specific contraindications for spinal and or epidural injections. The contraindications are similar to those when using any other epidural or spinal needle commercially sold or currently available.

PRECAUTIONS: Only an experienced trained physician/surgeon should use these medical needle assemblies. The precautions are similar to those epidural/spinal needles now available.

IV. Some Major Advantages And Benefits Of The Needle Design

The ordinary skilled practitioner in this art (i.e., the surgeon or physician) will recognize and appreciate the multiple singular advantages and unexpected benefits provided by the present invention. These include the following:

1. By passing the medical needle assembly from the primary incision site to the secondary external exit site, the possibility of inadvertently introducing bacteria is minimized greatly. This capability of markedly reducing the incidence of bacterial infections at the primary incision site is a long desired medical goal and of overwhelming benefit.

2. The possibility of seriously damaging the catheter, drain, or electrical wire leads with the sharp end tip of the epidural or spinal needle as occurs conventionally when the end tip emerges into the open channel of the surgical incision space is substantially reduced and effectively eliminated. This feature alone will diminish the complications often associated with this type of surgery.

3. This medical needle device provides a dual function: (i) When the needle hub is attached to the assembly, a syringe can be connected to the needle, which then can be used for aspiration or injection of fluid; and (ii) the needle hub can be used as a tunneling device, and the hub can be removed to allow the shaft to be passed from the primary incision. These features therefore eliminate the need for an additional instrument by which to generate a subcutaneous tunnel within the tissues of the patient.

4. The overall cost of the surgery is meaningfully reduced. Given the ever-increasing cost of medical care, and surgery in particular, this is not a trivial or insignificant effect.

5. The use of the medical needle device for subcutaneous tunneling obviates the conventional medical practice and need to create a rather large surgical incision that would otherwise be required when a separate tunneling instrument is used.

6. The patient experiences less pain and discomfort when the present medical needle assembly and methodology is employed.

The present invention is not to be restricted in scope nor limited in form except by the claims appended hereto:

What we claim is:

1. A safe method for surgically creating a tunnel subcutaneously through the tissues of a living subject from an open channel at a pre-existing primary incision site to a pre-chosen secondary external exit site, said safe method comprising the steps of:
 assembling a medical needle assembly comprising an elongated needle body including
  (i) a hollow shaft having fixed dimensions and configuration, at least one solid wall, an open internal cavity, and discrete first and second open ends,
  (ii) a sharp open tip formed at said first of said open ends, and
  (iii) engagement means disposed at said second of said open ends for at will engagement and disengagement of a needle hub, a removable at will needle hub including
  (a) a preformed hub structure having preset dimensions and configuration, at least one solid wall, at least one open lumen, and at least two discrete open hub ends,
  (b) attachment means disposed at one open end of said hub structure for on-demand attachment and detachment of said needle hub to said second open end of said needle body, and
  a fitted stylet configured to pass freely through and lie within said open internal cavity of said elongated needle body;
 introducing said sharp open tip of said assembled medical needle assembly into the open channel of the pre-existing primary incision site in the living subject;
 orienting said introduced sharp open tip of said assembled medical needle assembly within the open channel of the pre-existing primary incision site towards the secondary external exit site in the living subject, the secondary external exit site being pre-chosen to be adjacent and anatomically lateral to the primary incision site;
 inserting said oriented sharp open tip of said medical needle assembly into the subcutaneous tissues of the living subject;
 forcibly moving said inserted sharp open tip of said medical needle assembly through the subcutaneous tissues of the living subject until the pre-chosen secondary external exit site is reached; and
 piercing the skin at the pre-chosen secondary external exit site using said sharp open tip of said medical needle assembly such that said sharp open tip perforates the skin and becomes becomes exposed to the ambient environment.

2. A safe method for placing a tangible object having a known linear length and two distinct ends within a purposefully created subcutaneous tunnel which extends through the tissues of a living subject from an open channel at a pre-existing primary incision site to a pre-chosen secondary external exit site, said safe method comprising the steps of:
 assembling a medical needle assembly comprising an elongated needle body including
  (i) a hollow shaft having fixed dimensions and configuration, at least one solid wall, an open internal cavity, and discrete first and second open ends,
  (ii) a sharp open tip formed at said first of said open ends, and
  (iii) engagement means disposed at said second of said open ends for at will engagement and disengagement of a needle hub,
 a removable at will needle hub including
  (a) a preformed hub structure having preset dimensions and configuration, at least one solid wall, at least one open lumen, and at least two discrete open hub ends,
  (b) attachment means disposed at one open end of said hub structure for on-demand attachment and detachment of said needle hub to said second open end of said needle body, and
  a fitted stylet configured to pass freely through and lie within said open internal cavity of said elongated needle body;
 introducing said sharp open tip of said assembled medical needle assembly into the open channel of the pre-existing primary incision site in the living subject;
 orienting said introduced sharp open tip of said assembled medical needle assembly within the open channel of the pre-existing primary incision site towards the secondary external exit site in the living subject, the secondary external exit site being pre-chosen to lie adjacent and anatomically lateral to the primary incision site;

inserting said oriented sharp open tip of said assembled medical needle assembly present into the subcutaneous tissues of the living subject;

forcibly moving said inserted sharp open tip of said assembled medical needle assembly through the subcutaneous tissues of the living subject until the pre-chosen secondary external exit site is reached subcutaneously;

piercing through to the skin using said sharp open tip of said assembled medical needle assembly such that said sharp open tip perforates the skin and becomes externally exposed to the ambient environment at the pre-chosen secondary external exit site;

withdrawing said fitted stylet from said open internal cavity of said medical needle; then detaching said removable on-demand needle hub from said medical needle assembly such that said second open end of said elongated needle body becomes directly accessible;

passing one end of the tangible object into said accessible second open end and through said internal cavity of said elongated needle body such that said passed end exits from said sharp open tip of said elongated needle body and lies exposed to the ambient environment at the pre-chosen secondary external exit site; and then retracting and withdrawing said elongated needle body from the open channel of the pre-existing primary incision site, whereby the linear length of the long tangible object extends from the pre-existing primary incision site to the pre-chosen secondary external exit site within a subcutaneous tunnel.

3. The safe method as recited by claim 1 or 2 wherein said medical needle assembly is an epidural needle design suitable for accessing the epidural space of the spinal cord.

4. The safe method as recited by claim 1 or 2 wherein said medical needle assembly is a spinal needle design suitable for accessing the subarachnoid space of the spinal cord.

5. The safe method as recited by claim 1 or 2 wherein the long tangible object is selected from the group consisting of a catheter, a drain, and an electrical wire lead.

* * * * *